United States Patent
Nielsen et al.

(10) Patent No.: US 8,666,099 B2
(45) Date of Patent: Mar. 4, 2014

(54) HEARING AID AND A METHOD FOR ALLEVIATING TINNITUS USING A NOTCH FILTER

(71) Applicant: Widex A/S, Lynge (DK)

(72) Inventors: Jakob Nielsen, Copenhagen (DK); Georg Stiefenhofer, Lynge (DK); Mike Lind Rank, Farum (DK); Stine Kohrtz Andersen, Vanloese (DK)

(73) Assignee: Widex A/S, Lynge (DK)

( * ) Notice: Subject to any disclaimer, the term of this patent is extended or adjusted under 35 U.S.C. 154(b) by 0 days.

(21) Appl. No.: 13/650,173

(22) Filed: Oct. 12, 2012

(65) Prior Publication Data

US 2013/0039517 A1  Feb. 14, 2013

Related U.S. Application Data

(63) Continuation-in-part of application No. PCT/DK2010/050085, filed on Apr. 16, 2010.

(51) Int. Cl.
*H04R 25/00* (2006.01)

(52) U.S. Cl.
USPC .......................................... 381/317; 381/328

(58) Field of Classification Search
USPC ......................................................... 381/314
See application file for complete search history.

(56) References Cited

U.S. PATENT DOCUMENTS 6,816,599 B2   11/2004   Thiede et al.
2008/0123886 A1*  5/2008   Andersen et al. ............. 381/320

FOREIGN PATENT DOCUMENTS

| DE | 20110947 U1 | 12/2001 |
| DE | 10128642 A1 | 1/2002 |
| EP | 0897254 A2 | 2/1999 |
| EP | 1920632 B1 | 11/2009 |
| WO | 2008087157 A2 | 7/2008 |
| WO | 2011006681 A1 | 1/2011 |

OTHER PUBLICATIONS

International Search Report for PCT/DK2010/050085 dated Apr. 7, 2011.
Written Opinion of the International Searching Authority for PCT/DK2010/050085 for Mar. 29, 2011.
Pawel J. Jastreboff, PHD, "Instrumentation and tinnitus: A neurophysiological approach", Tinnitus Research XP 000628019, Hearing Instruments, vol. 45, No. 7, 1994.

* cited by examiner

*Primary Examiner* — Brian Ensey
*Assistant Examiner* — Katherine Faley
(74) *Attorney, Agent, or Firm* — Sughrue Mion, PLLC

(57) ABSTRACT

A hearing aid (62, 72, 82, 92, 102, 112) adapted for alleviating tinnitus of a user (75), comprises an audio input means (83), a signal processing unit (88, 98, 108, 118) and an output transducer (80). The hearing aid further comprises a band stop filter (87) arranged to match a tinnitus of the user and switching means (86, 116) and switch control means (84, 114) for controlling the switching of said band stop filter (87) into and out of the signal path between the audio input means (83) and the output transducer (80), in response to a predefined trigger event. The invention further provides a method of adjusting a hearing aid.

20 Claims, 6 Drawing Sheets

HEARING AID AND A METHOD FOR ALLEVIATING TINNITUS USING A NOTCH FILTER

RELATED APPLICATIONS

The present application is a continuation-in-part of application No. PCT/DK2010/050085, filed on Apr. 16, 2010, in Denmark and published as WO2011127930 A1.

BACKGROUND OF THE INVENTION

1. Field of the Invention

The present invention relates to hearing aids. The invention, more specifically, relates to a hearing aid having means for alleviating tinnitus. The invention further relates to a method for adjusting a hearing aid.

2. The Prior Art

A device for treating tinnitus is known from WO-A2-2008/087157. The device comprises a generator means for generating an audio signal and a transducer means for reproducing the audio signal having interposed between them a filter. The filter is matched to suppress the audio signal in an interval of frequencies around a dominant frequency of a tinnitus. WO-A2-2008/087157 also describes a method for matching the filter to enable the suppression by estimating the subjective intensity and the dominant frequency of tinnitus. The subjective intensity is estimated by means of an audiometric procedure, while the dominant frequency is estimated by means of the signal generator of the device.

This method implies that the frequencies used to estimate the subjective intensity and the frequencies identified by the estimation of the dominant frequency may differ from each other. This may result in that the peak frequency in the frequency spectrum of the estimated subjective intensity and the estimated dominant frequency differ from each other. This in turn has the implication that the matching of the filter is affected such that either an inconveniently large spectral width of the filter will be necessary or the tinnitus may not be sufficiently suppressed.

Furthermore, the known matching method is, due to its use of audiometric measurements and following dependence on extensive and complicated equipment, confined to be performed by qualified staff, thus rendering exploitation of the advantages related to the use of the matching procedure outside the laboratory rather cumbersome.

In a related method for alleviating tinnitus, a patient listens, on a regular basis, to music where the music is modified to contain no energy in the frequency range surrounding the, individually determined, tinnitus frequency of the patient. According to this method the patient chooses music that he or she finds enjoyable, and receives a recording of the music, which has been modified as described above. See "Listening to tailor-made notched music reduces tinnitus loudness and tinnitus-related auditory cortex activity", Proceedings of the National Academy of Sciences of the United States of America, Jan. 19, 2010 vol. 107 no. 3, pp. 1207-1210.

This method of tinnitus alleviation is inflexible insofar as the patient, as part of the alleviation, can only listen to the music that has been modified and stored on some audio media. This may especially be problematic since the method is a long term alleviation, which is partly based on the requirement that the patient finds the music enjoyable. Another problem arises if the audio media is lost, damaged or for some reason not brought along by the patient.

SUMMARY OF THE INVENTION

The present invention aims at providing a method for matching a hearing aid band stop filter, or notch filter, to a tinnitus, which method provides for an improved matching of the band stop filter to the tinnitus, and which method may be performed without or with a minimum of expensive and complicated equipment. The present invention further aims at providing a hearing aid having a band stop filter, or notch filter, and control means for selectively activating the band stop filter whenever music or other types of enjoyable or relaxing sounds are detected by the hearing aid, hereby providing the patient with the possibility of modifying, as described above, all the sounds that the patient has access to from his surroundings.

The invention, in a first aspect, provides a hearing aid adapted for alleviating tinnitus of a user, said hearing aid comprising an audio input means, a signal processing unit, an output transducer, a notch filter adapted for attenuating said audio signal at a frequency adapted to match a tinnitus of the user, switching means for switching said notch filter into a signal path formed by said audio input means, said signal processing unit and said output transducer, and out of said signal path, and switch control means, said switch control means being adapted for controlling the switching of said switching means in response to a predefined trigger event.

The invention, in a second aspect, provides a method for matching a hearing aid notch filter to a perceived tinnitus of a user of said hearing aid, comprising the steps of providing a hearing aid comprising a notch filter, using tones presented by said hearing aid to determine a characteristic frequency of said perceived tinnitus, setting a center frequency of said notch filter based on said determined characteristic frequency of said perceived tinnitus, using sound presented by said hearing aid to determine a spectral width of the perceived tinnitus of the hearing aid user, and setting a spectral width of said notch filter based on said determined spectral width of the perceived tinnitus of the hearing aid user.

Thereby a method for matching a hearing aid band stop filter to a tinnitus is provided with which the whole matching procedure may be performed using the same source to present audio signals to the user for determining the relevant parameters of the tinnitus. Consequently, the spectral width of the filter may be chosen to precisely match the frequency distribution of the tinnitus, hence filtering out as few frequencies as possible, while suppressing substantially all frequencies of the tinnitus and thereby affecting the sound image perceived by the user minimally.

The method according to the invention to match a hearing aid band stop filter to a tinnitus may be performed solely or at least substantially solely using a hearing aid and thereby enables alleviating the tinnitus of a user by means of a hearing aid. This in turn provides for alleviating tinnitus using simple and relatively cheaper equipment, which may advantageously be used outside of laboratory environments and during the user's everyday life.

In a preferred embodiment, the step of determining a spectral width of the perceived tinnitus comprises the steps of presenting a first plurality of audio signals to the user and determining by selection which of the plurality of signals exhibits the highest resemblance with the tinnitus. In a further preferred embodiment the step of determining a spectral width of the perceived tinnitus further comprises repeating the abovementioned steps with a second plurality of audio signals having a bandwidth being either narrower or wider than the bandwidth of the first plurality of signals. Preferably, the audio signals are narrow band noise signals.

In a preferred embodiment, the method comprises the further steps of determining the users hearing threshold and setting the tone at a predetermined output level with respect to the hearing threshold. Thereby the user's hearing threshold may be taken into account ensuring that the tone is presented at an output level audible to the user. Preferably, the predetermined output level corresponds substantially to the determined hearing threshold plus 8 to 16 dB, but not more than between 4 and 8 dB below the uncomfortable level (UCL). In case the dynamic range is not sufficient for the above given intervals the output level can be set at the center of the dynamic range, equally distant from the hearing threshold and the UCL.

As used herein, the term "uncomfortable level" or UCL means a level of the intensity of a tone above which the tone is no longer comfortable, but rather annoying or even painful, in the perception of the user. UCL is measured in dB.

In a preferred embodiment, the hearing threshold is measured using audio signals in a range of frequencies including at least 6 kHz and preferably both 6 and 8 kHz. Thereby it is ensured that the characteristic frequency of the tinnitus is within the range of frequencies measured in the hearing threshold measurement for the majority of people with tinnitus.

According to an embodiment, the step of determining the characteristic frequency of the tinnitus comprises the steps of performing a rough matching procedure followed by a fine matching procedure, wherein the rough matching procedure comprises the steps of adjusting a frequency of the tone to be stepwise falling or rising, stopping the adjustment when the user indicates that the tone matches the tinnitus, registering the frequency thus found and performing the steps at least once with the frequency falling and at least once with the frequency rising and until a pair of frequencies, found with a falling and rising tone respectively, fall within a range of about one octave, and the fine matching procedure comprises the steps of performing a falling procedure and a rising procedure, the falling procedure comprising the steps of presenting the tone at a frequency at the higher end of the range determined in the rough matching, adjusting the frequency of the tone stepwise, stopping the adjustment when the user has indicated that the tone has a lower frequency than the tinnitus, and registering the frequency thus found, and the rising procedure comprising the steps of starting the tone at a frequency at the lower end of the range determined in the rough matching, adjusting the frequency of the tone stepwise, stopping the adjustment when the user has indicated that the tone has a higher frequency than the tinnitus, and registering the frequency, thus found, and repeating the falling procedure and the rising procedure at least once each and until a pair of registered frequencies from the falling and rising procedure fall within a frequency range with a given bandwidth and determining the characteristic frequency of the tinnitus based on said frequency registrations, where the bandwidth is one third octave or less and preferably one sixth octave or less. Thereby the characteristic frequency of the tinnitus may be determined with a very high accuracy in a very simple manner.

The rough and fine matching procedures may be realized according to other embodiments that will be further described in the detailed part of the description.

According to still another embodiment, the rough and fine matching procedure is achieved in that the step of determining the characteristic frequency of the tinnitus comprises performing a free matching procedure comprising the steps of providing a tone with a continuously or stepwise variable frequency, providing a user controlled device for adjusting the frequency of the tone until the tone matches the tinnitus, registering the frequency thus found, repeating the previous steps at least once and stopping when two successive frequency registrations fall within a range of one third octave or less, preferably within a range of one sixth octave or less. Such a free matching procedure has the further advantage that it can be performed by the user without the need of any qualified personnel. Thereby a further advantage is achieved, namely that it becomes possible for the user to repeat the matching of the filter whenever necessary to ensure that the filter settings always match the tinnitus optimally.

Notwithstanding the above described methods for determining the characteristic frequency, the characteristic frequency of the tinnitus is preferably determined with an accuracy falling within one octave, preferably within one half octave, more preferably within one third octave, even more preferably within one sixth octave or less.

The tone presented by the hearing aid is any one of an internal tone generated in the hearing aid and an externally generated tone transmitted to and reproduced by the hearing aid.

In a preferred embodiment, the method comprises the further step of switching the band stop filter into or out from the hearing aid signal path in response to detection of any one of a predefined plurality of trigger events, thereby enabling selective activation or deactivation of the band stop filter.

As used herein the term "trigger event" generally means an event that when registered by the hearing aid would cause the hearing aid to shift hearing aid program or otherwise adjust its functionality.

Such trigger events may include but are not limited to trigger events selected from the group comprising the hearing aid detecting that the sound environment is primarily music, the hearing aid detecting that the sound environment is primarily speech, the hearing aid detecting that music is streamed directly from an external unit, and the hearing aid detecting that special synthesized tones generated internally in the hearing aid are presented to the user. In the following, special tones synthesized and generated internally in the hearing aid, in accordance with the methods described in e.g. U.S. Pat. No. 6,816,599 B2, will be denoted fractal music.

According to an embodiment the method comprises the further step of regularly adjusting the filter parameters based on measurements of an Auditory Steady-State Response (ASSR) of the hearing aid user. Thereby it becomes possible to ensure that the filter settings are continuously, or at intervals, matched to the user's tinnitus. In a preferred embodiment the ASSR measurements are used to qualitatively assess the strength of the perceived tinnitus.

According to various embodiments of the invention, the ASSR is measured by means of electroencephalography (EEG) or magnetoencephalography (MEG), and is preferably measured using the hearing aid. Patent application PCT/EP2010/051005, filed on Jan. 28, 2010, and published as WO-A-1-2011/006681 discloses a hearing aid having means for obtaining EEG measurements (see e.g. page 9, line 2, to page 11, line 9, and page 13, line 10, to page 14, line 20).

According to an embodiment, the method comprises the further step of transposing the frequencies removed by the filter such as to provide a frequency transposed signal. Frequency transposing is well known in the art of hearing aids. Further details may be found in e.g. EP-B1-1920632.

In a preferred embodiment, the method comprises the further step of logging parameters regarding the method in a memory unit, the parameters including but not being limited to parameters relating to the perceived tinnitus such as characteristic frequency and spectral width, parameters relating to the band stop filter such as center frequency and spectral width, parameters regarding the switching of the band stop filter into and out from the hearing aid signal path, parameters regarding the audio signal, the user's hearing threshold and UCL, and parameters regarding ASSR measurements. Thereby it becomes possible to monitor the process of alleviation by monitoring i.e. how the tinnitus develops, how, when and for how long the filter is used and so forth, and thereby to alter or adjust the alleviation in an appropriate manner.

The invention, in a third aspect, provides a method of adjusting the function of a hearing aid for alleviating perceived tinnitus for a user of the hearing aid, said hearing aid having audio input means, a signal processor, an output transducer, and a notch filter adapted to match the perceived tinnitus, comprising the steps of detecting the presence or the absence of a predetermined trigger event, in response to detection of the presence of the trigger event, switching the notch filter into a signal path formed by said audio input means, said signal processing unit and said output transducer, and in response to detection of the absence of the trigger event, switching the notch filter out of the signal path.

In a preferred embodiment the band stop filter is matched to the tinnitus by means of a method according to any one of the embodiments of the first aspect of the invention.

This provides a hearing aid with a band stop filter matched to a tinnitus with which the advantages of the abovementioned method may be readily achieved.

Further embodiments and advantages of such a hearing aid are given in the dependent claims, and in the detailed description following below.

BRIEF DESCRIPTION OF THE DRAWINGS

The invention will now be described in further detail based on non-limiting exemplary embodiments, and with reference to the drawings. In the drawings.

DETAILED DESCRIPTION OF THE INVENTION

Figure 1:
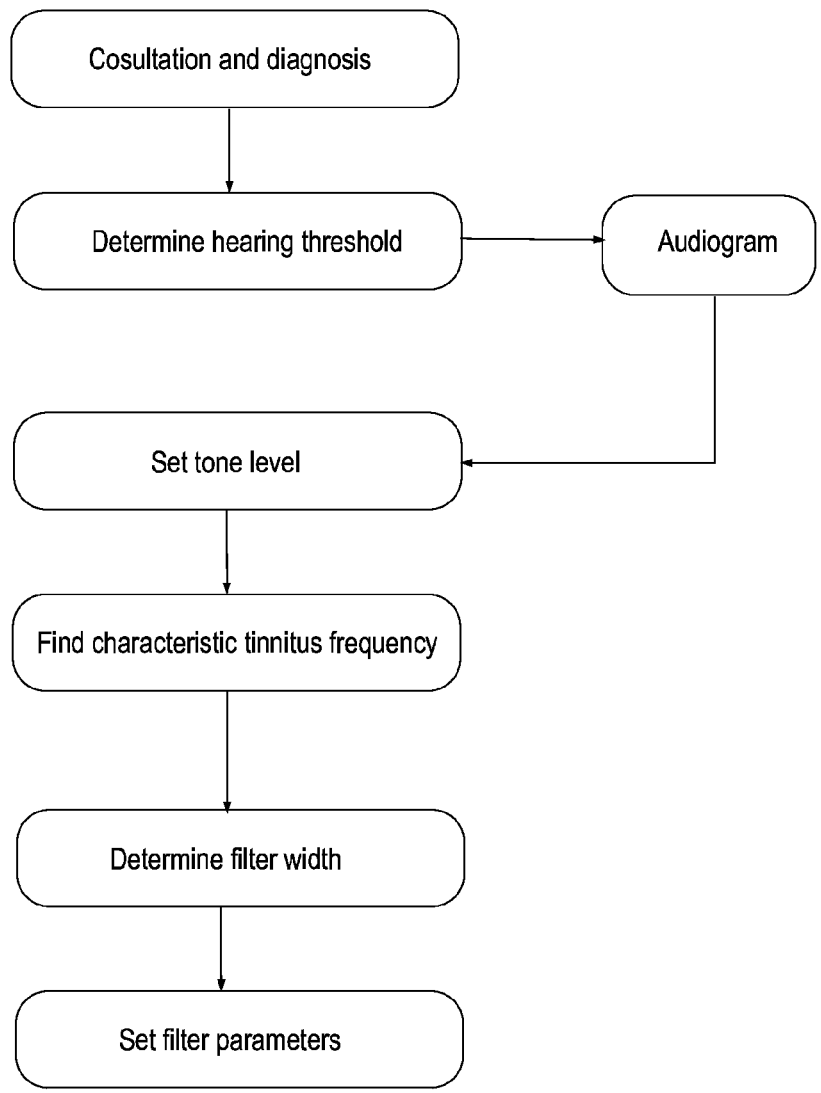
FIG. 1 is a diagram illustrating the steps of an embodiment of a method according to a first aspect of the invention.

FIG. 1 illustrates an embodiment of a method for matching a hearing aid band stop filter to a tinnitus of a user according to the invention in which the user's hearing threshold may be taken into account. It is noted that the method according to the invention may also be performed without taking into account the user's hearing threshold.

As shown in FIG. 1 a first step taking place ahead of the actual method according to the invention is illustrated. In this step, denoted consultation and diagnosis, qualified personnel, such as an ENT (Ear-Nose-Throat specialist) or audiologist, is consulted in order to diagnose the presence of tinnitus.

The next step illustrated is the optional step of determining the hearing threshold (HTL). The HTL is preferably determined prior to the actual matching procedure, and is typically performed by an audiologist using audiometric techniques known per se. In order to ensure that the tinnitus frequency is within the range of frequencies measured in the HTL measurement, the frequencies 6 kHz and 8 kHz are preferably included. The result of the HTL measurement is an audiogram that may be used in subsequent steps.

Next, the level of the tone or tones used in the matching procedure and presented to the user by means of the hearing aid is set to a predetermined output level and frequency.

If the HTL has been measured, the output level of the tone is chosen with respect to the measured HTL, and is preferably set to the HTL plus 8 to 16 dB, preferably the HTL plus 12 dB, but not more than a range between 4 and 8 dB below the UCL, preferably about 6 dB below the UCL. The HTL for frequencies not measured in the audiogram are preferably linearly interpolated with respect to the measured frequencies.

Then the characteristic frequency of the tinnitus is to be determined in order to enable setting the center frequency of the band stop filter. The matching of the tinnitus frequency is executed in two steps as a rough matching procedure followed by a fine matching procedure and is described in detail below, cf. FIGS. 2 and 3. Alternatively, a free matching procedure could be performed, cf. FIG. 4.

Next the spectral width of the band stop filter is to be determined. In this step it is verified that the tinnitus is tonal by presenting different sounds to the user by means of the hearing aid, the sounds having frequencies around the found characteristic frequency to determine the spectral width of the perceived tinnitus. Preferably, the sounds are in the form of narrow band noise signals. The procedure for determining the spectral width of the perceived tinnitus is described in detail below, cf. FIG. 5.

Finally the parameters of the band stop filter are set in accordance with the found characteristic frequency and spectral width of the perceived tinnitus. The band stop filter parameters include center frequency (being set to the characteristic frequency) and spectral width (being set in accordance with the determined spectral width of the perceived tinnitus). Other band stop filter parameters include e.g. filter attenuation.

According to various embodiments according to the invention the band stop filter attenuates in the range of 20 to 40 dB at the center frequency, preferably about 30 dB. According to a further preferred embodiment the band stop filter is realized as an Infinite Impulse Response (IIR) filter. The filter order of the band stop filter depends on the selected spectral width such that a fourth order filter is preferred for providing a spectral width of one octave, sixth order filter is preferred for providing a spectral width of one half of an octave and an eighth order filter is preferred for providing a spectral width of one third of an octave.

Figure 2:
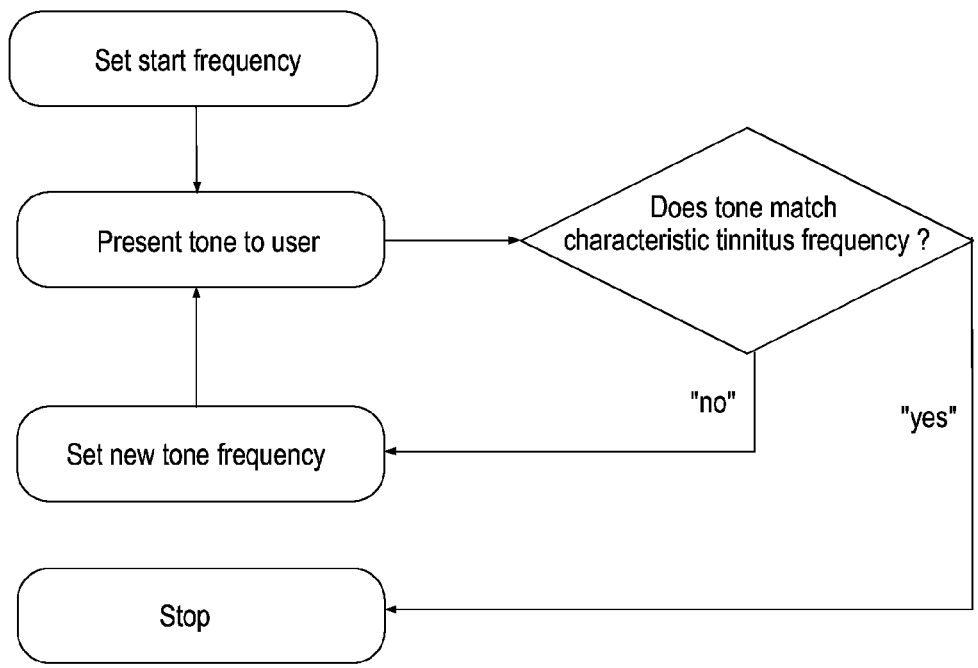
FIG. 2 is a diagram illustrating selected steps of a rough matching procedure for determining the characteristic frequency of a tinnitus in a method according to an embodiment of the invention.

Turning to FIG. 2 selected steps of a rough matching procedure for determining the characteristic frequency of the tinnitus are illustrated, according to an embodiment of the invention.

The aim of the rough matching procedure is to roughly locate the frequency of the tinnitus. This is done by presenting to the user sequences of tones with rising or falling frequencies. The user is instructed to stop the procedure when the frequency of the played tone matches the tinnitus best.

The rough matching procedure may be performed both with continuously or stepwise rising and falling sequences of tones and different start frequencies, respectively. Preferably, the start frequency for a rising sequence is 100 Hz, while the start frequency for a falling sequence is 8 kHz.

Preferably, the next frequency to be played for the user is derived as:

$$f(\text{next}) = f(\text{previous}) * \left(\sqrt[12]{2}\right)^5 f(\text{next}) = f(\text{previous}) * \left(\sqrt[12]{2}\right)^5$$

for a rising sequence and as:

$$f(\text{next}) = f(\text{previous}) * 1 / \left(\sqrt[12]{2}\right)^5 f(\text{previous}) * 1 / \left(\sqrt[12]{2}\right)^5$$

for a falling sequence.

Thus the formula used for deriving the next frequency for the rising sequence includes multiplying the previous frequency with a constant defined as the twelfth root of two raised to the power of five. For the falling sequence the next frequency is derived by dividing the previous frequency with the constant defined as the twelfth root of two raised to the power of five.

Falling and rising sequences are repeated until a pair of frequencies, found with a falling and rising tone respectively, fall within a range of one octave.

Figure 3:
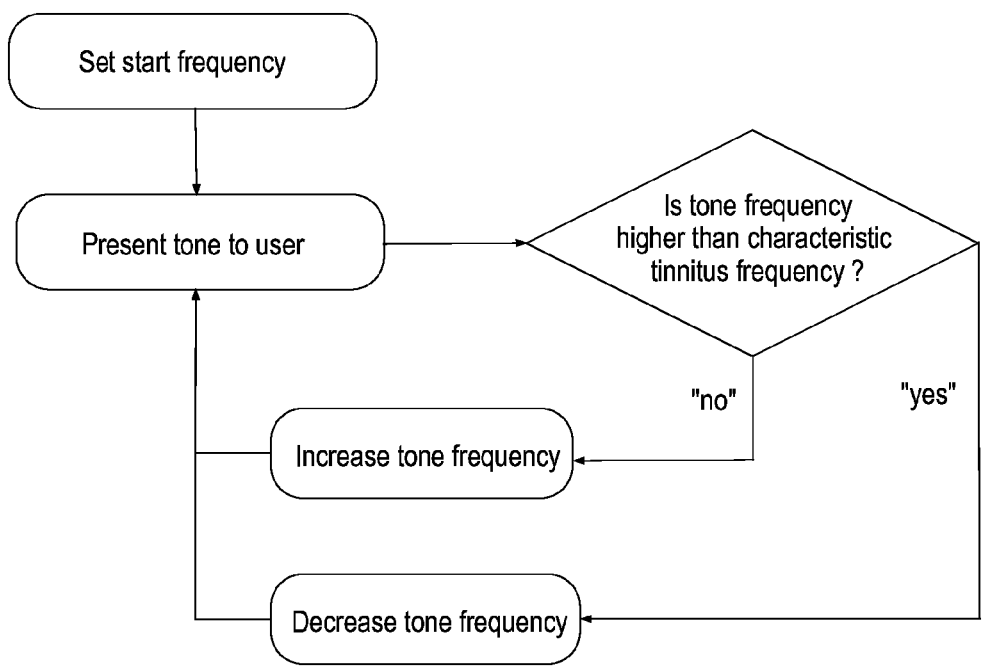
FIG. 3 is a diagram illustrating selected steps of a fine matching procedure for determining the characteristic frequency of a tinnitus in a method according to an embodiment of the invention.

Turning to FIG. 3 selected steps of a fine matching procedure, according to an embodiment, similar to the above described rough matching procedure are illustrated.

The aim of the fine matching procedure is to locate the characteristic frequency with a higher accuracy. Again two sequences of tones are presented to the user, one sequence with an initially falling frequency and one with an initially rising frequency. Thus the fine matching procedure can be described as comprising a falling procedure in which the sequence of tones presented to the user, at least initially, have a falling frequency, and a rising procedure in which the sequence of tones presented to the user, at least initially have a rising frequency.

The rising procedure comprises the following steps:

Present a tone at a frequency substantially equal to the lower edge of the frequency range found in the rough matching procedure.

Go up in frequency continuously or in intervals, preferably in intervals given as:

$$f(\text{next}) = f(\text{previous}) * 2^{\left(\frac{7}{39}\right)} f(\text{next}) = f(\text{previous}) * \left(\sqrt[20]{2}\right)^4.$$

Go down in frequency continuously or in intervals, preferably in intervals given as:

$$f(\text{next}) = f(\text{previous}) * 1 / 2^{\left(\frac{2}{39}\right)}.$$

Thus the formula used for deriving the next frequency for the rising sequence includes multiplying the previous frequency with a constant defined as two raised to the power of seven divided by 39 (when going up in frequency) and includes dividing the previous frequency with a constant defined as two raised to the power of two divided by 39 (when going down in frequency).

Similarly, the falling procedure comprises the following steps:

Present the tone at a frequency substantially equal to the higher edge of the frequency range found in the rough matching procedure.

Go up in frequency continuously or in intervals, preferably in intervals given as:

$$f(\text{next}) = f(\text{previous}) * 2^{\left(\frac{2}{39}\right)} f(\text{next}) = f(\text{previous}) * 1 / \left(\sqrt[20]{2}\right) f(\text{next}) = f(\text{previous}) * 1 / \left(\sqrt[20]{2}\right).$$

Go down in frequency continuously or in intervals, preferably in intervals given as:

$$f(\text{next}) = f(\text{previous}) * 1 / 2^{\left(\frac{7}{39}\right)}.$$

Thus the formula used for deriving the next frequency for the falling sequence includes multiplying the previous frequency with a factor defined as two raised to the power of two divided by 39 (when going up in frequency) and includes dividing the previous frequency with a factor defined as two raised to the power of seven divided by 39 (when going down in frequency). The step sizes, i.e. the factors $$2^{\left(\frac{2}{39}\right)}$$

(two raised to the power of two divided by 39) and $$2^{\left(\frac{7}{39}\right)}$$

(two raised to the power of seven divided by 39) for altering the frequencies are chosen, such that seen on a musical scale a played tone in one octave range cannot be played in the next octave range again. In other words the step sizes are chosen such that a precise doubling or halving of the tone frequencies is not possible. It is a further advantage that by going one step up or down in frequency from an initial frequency, one can not return to the initial frequency by going in the other direction.

Whenever the direction of going up or down in frequency is changed a so called "reversal point" occurs. Both the falling and the rising procedure stop when ten reversals have occurred. The frequencies found by the two procedures are then determined by averaging the frequency values of the reversal points, but disregarding the first four reversals.

Both the rising and the falling procedure are repeated until the found frequencies for both the falling and rising procedure are within at least one half an octave and preferably within one third of an octave. The characteristic tinnitus frequency is then determined by averaging the found frequencies for both the falling and rising procedure.

According to a further embodiment, the step sizes for going up and going down in frequency are identical and the factor is two raised to the power of two divided by 39.

According to an embodiment, the tones are presented for the user with a duration of about three seconds.

According to further embodiments, the concept of reversal points is also used in the rough matching procedure. According to an embodiment, the rough matching starts at a frequency of 100 Hz and proceeds by going up and down in frequency dependent on the users indications of whether the frequency of the presented tone is higher than the characteristic tinnitus frequency. The procedure stops when four reversals have occurred, and the fourth reversal point is used as starting point for a fine matching procedure that only includes a rising procedure. According to an alternative embodiment, the rough matching starts at a frequency of 8 kHz, and the fine matching procedure only includes a falling procedure.

Figure 4:
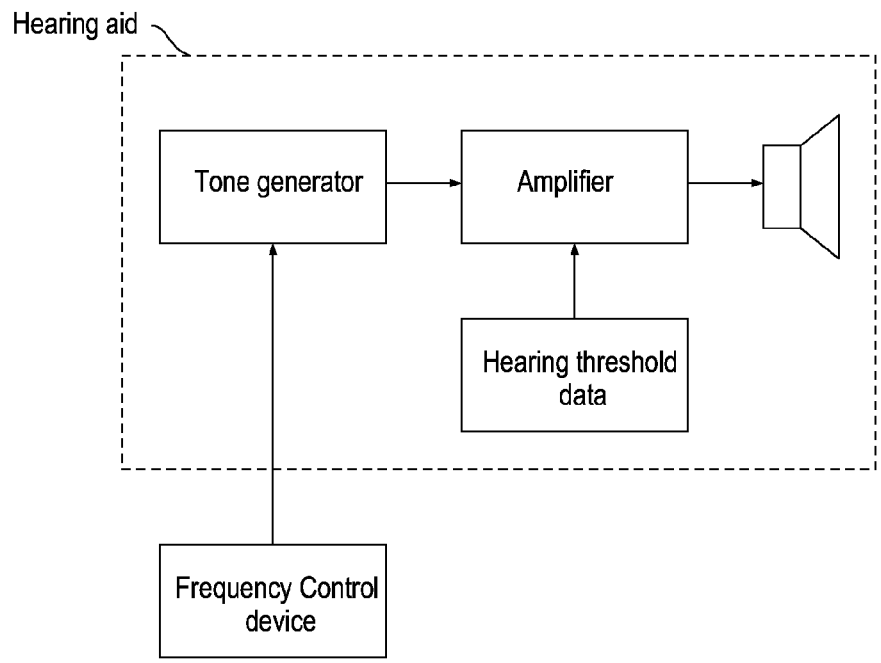
FIG. 4 illustrates a highly schematic illustration of selected parts of a hearing aid system adapted for a free matching procedure for determining the characteristic frequency of a tinnitus in a method according to an embodiment of the invention.

FIG. 4 shows a highly schematic illustration of selected parts of a hearing aid system adapted for an alternative method for finding the characteristic frequency of the tinnitus, in the form of a free matching procedure. In a free matching procedure the hearing aid user is presented with a tone with a continuously or stepwise variable frequency, and uses a device to freely adjust the frequency of the tone. Such a device could be the remote control of the hearing aid, a graphical user interface (GUI) on a computer or another hardware device. Where the HTL has been measured, the output level of the tone may automatically compensate for the user's HTL to ensure audibility.

The user freely adjusts (i.e. lowers or rises) the frequency until the user thinks the frequency matches his or her tinnitus, the user registers the frequency thus found, repeats the previous steps at least once and stops when two successive frequency registrations fall within a range of one third octave or less, preferably within a range of one sixth octave or less.

Obviously, any one of the rough, fine and free matching procedures may be repeated until the frequencies found fall within a narrower octave interval than those stated above, e.g. one eighth or one twelfth octave.

Figure 5:
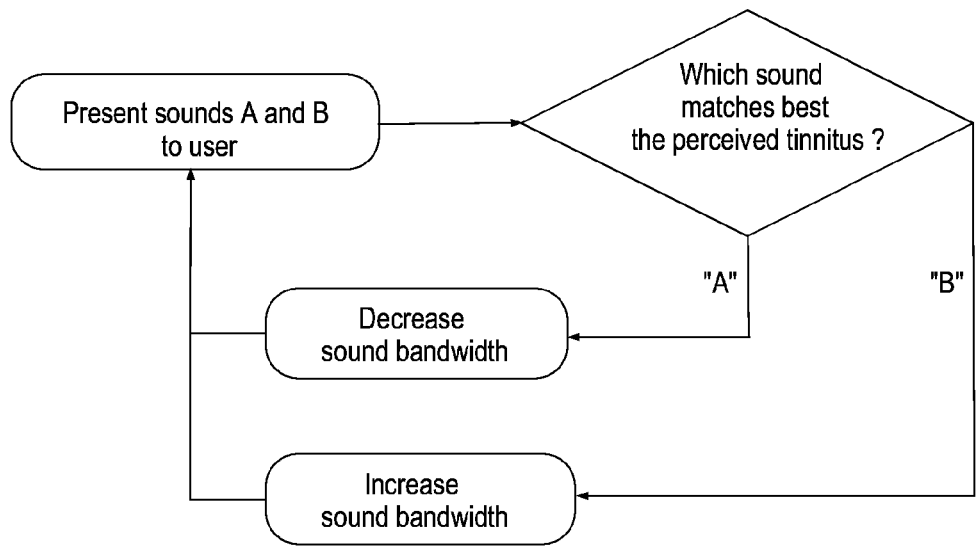
FIG. 5 is a diagram illustrating selected steps of determining a spectral width of a perceived tinnitus in a method according to an embodiment of the invention.

FIG. 5 illustrates a procedure for determining the spectral width of the perceived tinnitus of the user.

In order to determine the spectral width of the perceived tinnitus the user is presented for multiple audio signals, preferably audio signals with different bandwidths centered on the characteristic frequency found in the matching procedure. The patient is asked to determine which audio signal matches the tinnitus best. A preferred way of realizing this is by means of a selection procedure. As illustrated in FIG. 5 such a selection procedure may be a so-called ABX-procedure, in which two audio signals "A" and "B" are presented to the user, audio signal "A" having a narrower bandwidth than audio signal "B". The ABX procedure is well known in the art of detection theory, see e.g. "Detection theory: a user's guide" by Neil A. Macmillan and C. Douglas Creelman, Lawrence Erlbaum Associates, 2005.

Depending on which audio signal the user chooses to match the tinnitus best, the next iteration of the procedure comprises presenting audio signals with either narrower or wider bandwidths than the preceding audio signal. If the user chooses the audio signal "A" with the narrower bandwidth, the next iteration comprises presenting audio signals with a narrower bandwidth. If the user chooses the audio signal "B" with the wider bandwidth, the next iteration comprises presenting audio signals with a wider bandwidth.

The procedure is stopped when the bandwidth of the audio signal chosen by the user is below a given threshold.

According to another embodiment the spectral width of the perceived tinnitus of the user is determined by a method where the start bandwidths for signals "A" and "B" are ¼ octave and ½ octave and are narrowed or widened by 1/24 octave in each iteration, but with a minimum signal bandwidth referring to a pure tone and a maximum signal bandwidth of ¾ octave. Similar to the previously described rising and falling method for the fine matching, the number of reversals is counted. A reversal is again defined as a change in direction, i.e. going from wider bandwidth to a narrower bandwidth and vice versa. The procedure is finished when either of the following three criteria is fulfilled: six reversals have occurred, the patient has nine times in a row chosen the narrower bandwidth signal, resulting in the procedure presenting signal "A" with the minimum bandwidth, the patient has nine times in a row chosen the wider bandwidth signal, resulting in the procedure presenting signal "B" with the maximum bandwidth.

In the first case the spectral width of the perceived tinnitus of the user is determined as the average of the bandwidths of signal "A" and "B" at the final six reversals. In the second case the perceived tinnitus of the user is determined as the minimum bandwidth, and in the third case the spectral width of the perceived tinnitus of the user is determined as being wider than the maximum signal bandwidth.

If the found spectral width of the perceived tinnitus of the user is equal to or below ¼ octave, the band stop filter can be set to a bandwidth of ⅓ octave. In case the found spectral width of the perceived tinnitus of the user is equal to or below ⅓ octave, the band stop filter can be set to a bandwidth of ½ octave. In case the found spectral width of the perceived tinnitus of the user is equal to or below ½ octave, the band stop filter can be set to a bandwidth of one octave.

In case the found spectral width of the perceived tinnitus of the user is wider than ½ octave, it is recommended to consult qualified personnel since the tonal character of the tinnitus cannot be guaranteed and therefore the determined characteristic tinnitus frequency may not be the right choice as the center frequency for the band stop filter. Thus according to this embodiment, the band stop filter bandwidth it set to be wider than the found spectral width of the perceived tinnitus of the user. Hereby the sensitivity to the precision of the determination of the center frequency of the band stop filter relative to the characteristic tinnitus frequency is reduced.

According to yet another embodiment, the spectral width of the perceived tinnitus of the user is determined by running either of the above described methods for fine matching of the characteristic tinnitus frequency at least five times and calculating the standard deviation of the ten found characteristic tinnitus frequencies (e.g. five frequencies from the rising part of the method and five frequencies from the falling part). In case the standard deviation is equal to or below ¼ octave the bandwidth of the band stop filter can be set to ⅓ octave, in case the standard deviation is equal to or below ⅓ octave the bandwidth of the band stop filter can be set to ½ octave, in case the standard deviation is equal to or below ½ octave the bandwidth of the band stop filter can be set to one octave, and for standard deviations larger than ½ octave it is recommended to consult qualified personnel since the tonal character of the tinnitus cannot be guaranteed and therefore the determined characteristic tinnitus frequency may not be the right choice as the center frequency for the band stop filter.

The tone used for determining the characteristic frequency may be an internal tone generated in the hearing aid, in which case so-called on-the-fly matching is possible, that is the hearing aid may be matched whenever needed without external devices being necessary. Hence matching after measuring a change in the tinnitus or after an adjustment of the hearing aid may be performed readily without delay.

Alternatively the tone may be an external tone generated in an external device and transmitted to and reproduced by the hearing aid. This would enable matching performed in a user-controlled environment, e.g. as part of a so-called self-fitting procedure in which the user performs the fitting without the need of an audiologist, or as part of a fitting procedure in a so-called user environment.

A possible alternative, regardless of the source of the tone, is a remote controlled band stop filter adjustment—that is a matching procedure performed by means of a hearing aid remote control. Obviously, the matching may also be performed as an audiologist-assisted matching procedure, e.g. as part of a standard fitting procedure known per se.

In a further step of the method, the band stop filter may be switched into or out of the hearing aid signal path in response to detection of a trigger event. Examples on such trigger events are given in the introductory part of the description.

When the band stop filter is switched into the hearing aid signal path, audio signals filtered by means of the band stop filter and presented for the hearing aid user have been shown to be particularly efficient for alleviating tinnitus, when the audio signals are music or similar relaxing sounds. Therefore it is preferred to be able to switch the band stop filter into the hearing aid signal path in response to the hearing aid detecting an audio signal comprising mainly music. The music audio signal can be received from a variety of hearing aid audio inputs such as a microphone, a telecoil, a wireless link adapted for audio streaming or internally generated fractal music. Hereby sounds for alleviating tinnitus can be provided for the hearing aid user in a simple manner that does not require synthetic generation of the sounds for the tinnitus alleviation.

It is also particularly useful to be able to switch the band stop filter out of the hearing aid signal path when the hearing aid detects a sound environment primarily being speech. Thereby it is avoided that the band stop filter compromises the hearing aid user's ability to understand the speech.

During a period of alleviating the user's tinnitus, the tinnitus parameters may change, and it may therefore be necessary to adjust the band stop filter parameters in order to continuously ensure an optimal alleviation. Such an adjustment may obviously be performed by simply repeating the matching method according to the invention at intervals without knowing on pre-hand whether the tinnitus parameters have actually changed.

It is preferred, however, to first acquire a measurement giving an indication on whether the tinnitus parameters have changed according to the user's perception of his or her tinnitus and base the adjustment of the band stop filter on this measurement. Such a measurement may be acquired by measuring the user's Auditory Steady-State Response (ASSR). Thereby an adaptive band stop filter may be obtained.

The ASSR is preferably measured by means of electroencephalography (EEG) or magnetoencephalography (MEG) in methods being known in the art per se.

The EEG or MEG measurement is preferably made by means of the hearing aid. Thereby the user's perception of his or her tinnitus, i.e. whether it is unchanged, improved or deteriorated, may be evaluated and the band stop filter parameters (center frequency, width, damping etc.) may be adjusted accordingly, either manually, e.g. by the user or an audiologist, or automatically, e.g. by means of the hearing aid itself by executing a specially adapted hearing aid program.

Another particularly useful feature is to be able to log parameters regarding the method according to the invention in a memory unit, the parameters including but not being limited to parameters such as tone output level and frequency, characteristic frequency and spectral width of the perceived tinnitus, filter parameters, parameters regarding the switching on and off of the band stop filter, the user's hearing threshold and UCL and parameters regarding ASSR measurements.

Thereby it becomes possible to monitor both the progress of the method and, which is more essential, the progress and effects of the tinnitus alleviation by evaluating the logged data monitoring i.e. how the tinnitus develops, how, when and for how long the filter is used and so forth, and thereby to alter or adjust the alleviation in an appropriate manner. Furthermore, logging data enables the possibility of giving feedback regarding the alleviation to the user, an audiologist or another relevant person.

The method according to the invention may be implemented in a hearing aid as a separate hearing aid band stop filter matching program or as a dedicated tinnitus hearing aid program, preferably comprising an alleviation program. Such a program may be stored in a memory of the hearing aid and be executed by means of a signal processing unit of the hearing aid.

Such a hearing aid program may comprise any one or more of the following program components, without being limited thereto:

- a band stop filter program for implementing a method according to the invention,
- a fractal music relaxation program
- a first special music program for playing fractal music as tinnitus masker around the characteristic frequency,
- a second special music program for playing band stop filtered fractal music
- a tinnitus alleviation programme, preferably for long term alleviation, enabling, i.e. controlling, the daily use of the band stop filter, switching the band stop filter into and out from the hearing aid signal path, providing feedback to the user, e.g. as speech messages such as "You need one more hour of tinnitus alleviation today", providing a programmable timer, evaluating the user's tinnitus at intervals, e.g. once per month, and based on the evaluation providing feedback to the user regarding the progress of the alleviation, providing feedback to the audiologist, e.g. regarding whether the choice of tinnitus program is appropriate, and adjusting band stop filter parameters.

Figure 6:
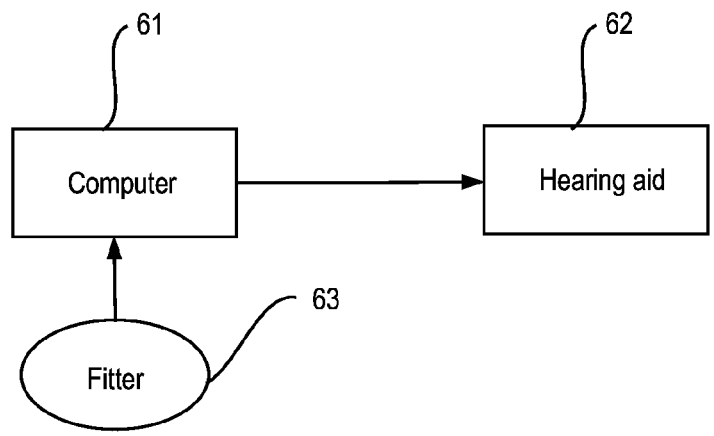
FIG. 6 illustrates a hearing aid according to an embodiment of the invention in association with the equipment necessary for carrying out a method according to an embodiment of the invention.

FIG. 6 shows the equipment necessary for carrying out a method according to the invention in the embodiment as illustrated in FIG. 1 and optionally including the above described step of switching on or off the band stop filter in response to detecting a trigger event in the case where the matching procedure is carried out as part of a fitting session assisted by professional staff such as an audiologist or fitter 63.

The equipment includes a hearing aid 62 according to the second aspect of the invention. Such a hearing aid 62 will be described in further detail below, but generally comprises an input transducer, a signal processing unit, an output transducer and a band stop filter. Preferably, the hearing aid 62 also comprises a switch and switch control means for controlling the activation and de-activation of said band stop filter.

The hearing aid 62 is in wireless or wired communication with suitable hearing aid fitting hardware, such as a computer 61, comprising fitting software. Depending on the electronics and software present in the computer 61 and the hearing aid 62, respectively, the method may be carried out wholly or partly by the computer 61 or by the hearing aid 62.

Figure 7:
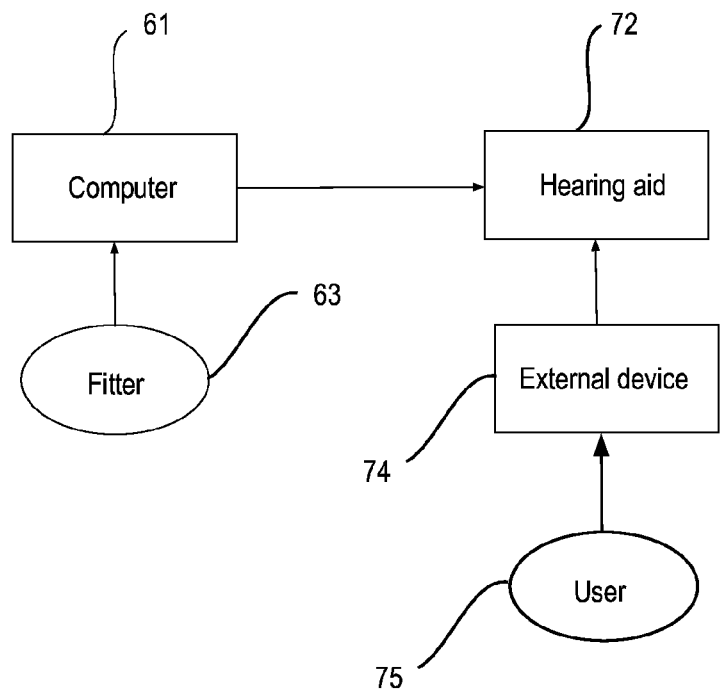
FIG. 7 illustrates a hearing aid according to an embodiment of the invention in association with the equipment necessary for enabling the user to carry out, on his or her own, a method according to an embodiment of the invention.

FIG. 7 shows the equipment necessary for carrying out a method according to the invention in the embodiment as illustrated in FIG. 1, and optionally including the above described step of activating and de-activating the band stop filter, in the case where the matching procedure is carried out by the user 75 on his or her own. To this end the hearing aid 72 is supplied with an external device 74, such as a hearing aid remote control, which is operated by the user 75, adapted for wireless or wired data communication with the hearing aid 72 and intended for carrying out a free matching procedure as described above in connection with FIG. 4.

In the following a hearing aid according to the second aspect of the invention will be described with reference to FIGS. 8, 9 and 10.

Figure 8:
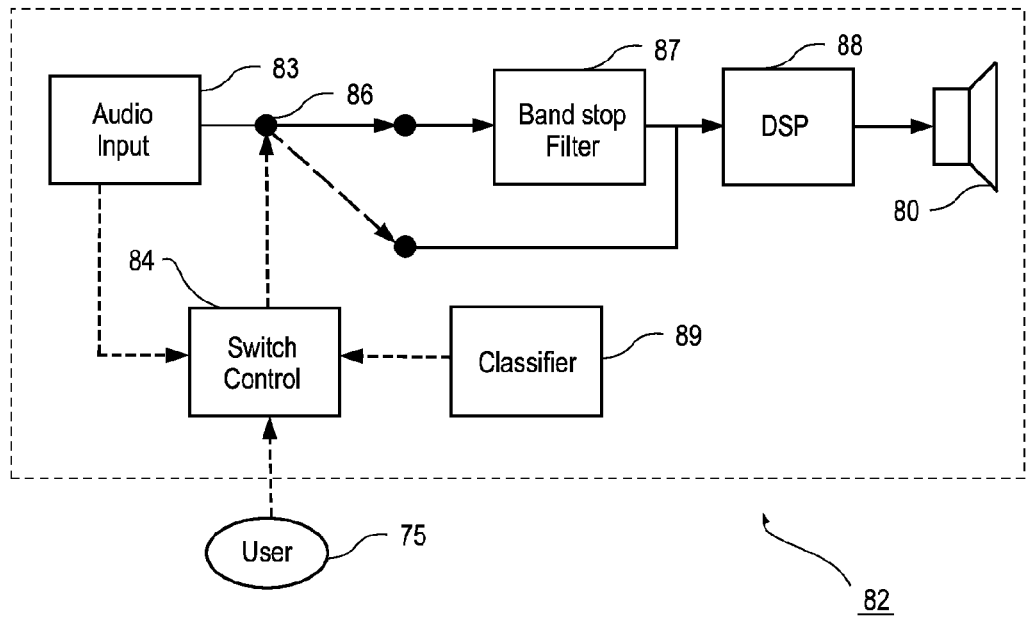
FIG. 8 illustrates highly schematically selected parts of a hearing aid according to a first embodiment of the invention.

FIG. 8 shows highly schematically selected parts of a hearing aid according to a first embodiment of the second aspect of the invention. The hearing aid 82 comprises an audio input 83 providing an audio signal, a digital signal processing unit (DSP) 88, an output transducer shown as a speaker 80, and a band stop filter 87.

The audio signals provided by the audio input 83 may be generated internally in the hearing aid or be generated externally and transmitted to and reproduced by the hearing aid. Fractal music may be generated internally in the hearing aid or the audio signals may be transmitted from an external unit such as a computer, television or mp3 player and to the hearing aid using e.g. telecoils or wireless data links, or the hearing aid may be operated in standard mode with the microphone providing the audio signals from the surroundings. Preferably, the audio signals are normal music or fractal music, as the latter type of music may be particularly useful for alleviating tinnitus when filtered.

The hearing aid 82 further comprises a switch control 84 controlling a switch 86 arranged for switching the band stop filter into or out from the hearing aid signal path in response to detection of a trigger events. In practice the switch may be set to transmit an audio signal from the audio input 83 through the band stop filter 87 and on to the DSP 88 or alternatively directly to the DSP 88 from the audio input. The output of the DSP 88 is transmitted to the output transducer 80. The switch control 84 is in turn controlled automatically by a classifier 89 or DSP 88 or controlled manually by the user 75, additionally the control may be based on the selected type of audio input.

According to an embodiment the classifier 89 is adapted to perform speech detection and the switch control 84 is adapted to automatically switch the band stop filter 87 out from the hearing aid signal path when the classifier 89 detects speech.

Figure 9:
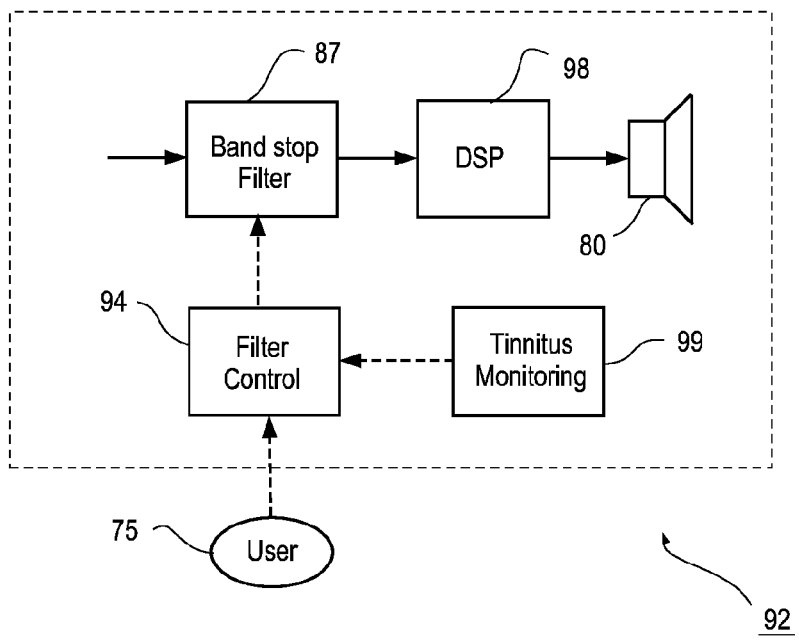
FIG. 9 illustrates highly schematically selected parts of a hearing aid according to a second embodiment of the of the invention.

FIG. 9 shows highly schematically selected parts of a hearing aid according to a second embodiment of the second aspect of the invention. The hearing aid 92 may in addition to the components shown in FIG. 9 comprise any of the components described above in connection with FIG. 8.

The hearing aid 92 further comprises a filter control means 94 for controlling an adaptation of said band stop filter in response to a registered change in the perceived strength of the tinnitus, and a tinnitus monitoring means 99 for monitoring the strength of the perceived tinnitus. The filter control means 94 may comprise a classifier and it may be a part of the DSP 98.

The tinnitus monitoring means 99 preferably registers changes in the strength of the perceived tinnitus based on measurements of an Auditory Steady-State Response (ASSR) of the user 75. The ASSR is preferably measured by means of EEG or MEG. The tinnitus monitoring means 99 preferably comprises electrodes adapted for detecting brain signals, such as EEG-signals, for measuring said ASSR. Such electrodes may be placed on or imbedded in the surface of the hearing aid 92, or may be external electrodes, such as e.g. scalp electrodes of an EEG-measurement system known per se. Alternatively, the tinnitus monitoring means 99 may comprise means for measuring an MEG, such as a Magnetic Resonance Imaging (MRI) unit.

According to an embodiment, the tinnitus monitoring means can be used to determine when the strength of the perceived tinnitus is so small that the band stop filter can be switched out from the hearing aid signal path. According to another embodiment the output from the tinnitus monitoring means is logged and stored in a data memory.

Figure 10:
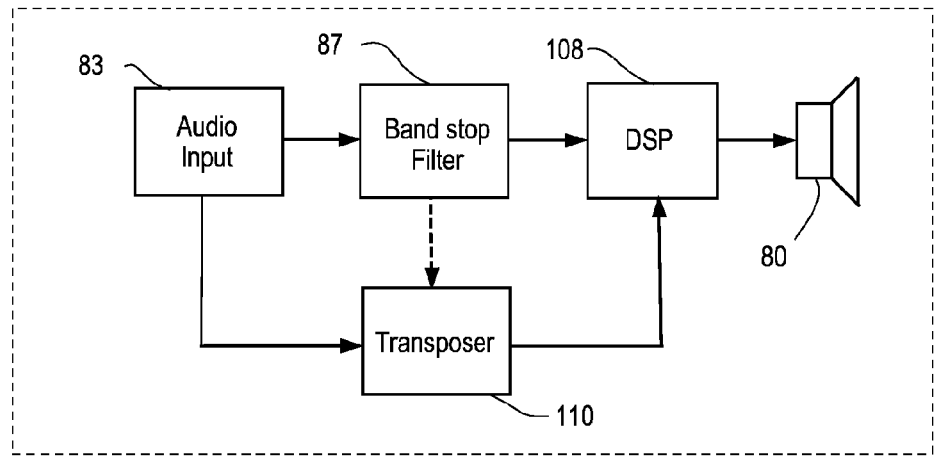
FIG. 10 illustrates highly schematically selected parts of a hearing aid according to a third embodiment of the invention.

FIG. 10 shows highly schematically selected parts of a hearing aid according to a third embodiment of the second aspect of the invention. The hearing aid 102 comprises an audio input 83 providing an audio signal, a band stop filter 87, a DSP 108, a speaker 80 and a transposer 110. The audio signal is fed to the band stop filter 87 and to the input of the transposer 110. Hereby the band stop filter 87 removes a certain band of frequencies from the audio signal to create a band stop filtered audio signal, and the transposer 110 transposes that same band of frequencies in the audio signal to create a frequency transposed audio signal. The band stop filtered audio signal and the frequency transposed audio signal are fed to the DSP 108, where the signals are added and further processed. Hereby it becomes possible to have the band stop filter switched into the hearing aid signal path, even in the presence of speech, without compromising speech intelligibility too much if at all.

The hearing aid 102 may in addition to the components shown in FIG. 10 comprise any of the components described above in connection with FIGS. 8 and 9.

Figure 11:
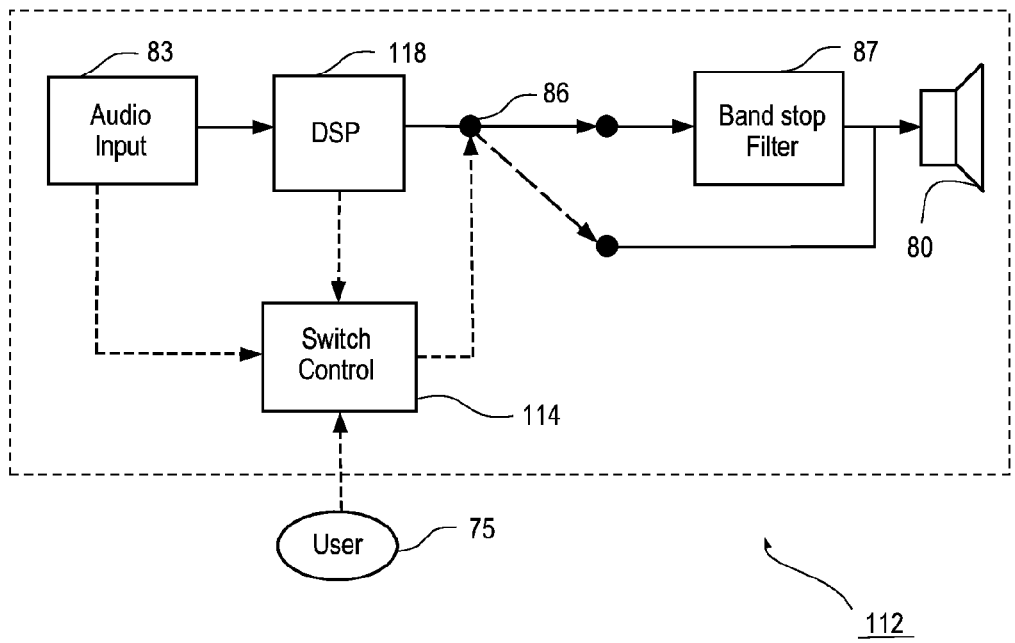
FIG. 11 illustrates highly schematically selected parts of a hearing aid according to a fourth embodiment of invention.

FIG. 11 shows highly schematically selected parts of a hearing aid according to a fourth embodiment of the second aspect of the invention. The hearing aid 112 comprises an audio input 83, a switch 86, switch control means 114, a band stop filter 87, a digital signal processor (DSP) 118 and a speaker 80. According to this embodiment the switch 116 and band stop filter 87 are positioned downstream of the digital signal processor and upstream of the speaker. Hereby the band stop filter will not have any negative impact on the various noise suppressing and speech intelligibility enhancing algorithms in the digital signal processor.

The hearing aid 112 may in addition to the components shown in FIG. 11 comprise any of the components described above in connection with FIGS. 8, 9 and 10.

Furthermore, in a not shown embodiment, a hearing aid according to the second aspect of the invention may comprise a means for logging data, such as a memory. Such a data logging means may be a part of the DSP or be a separate component of the hearing aid. It may also be an external unit, such as e.g. a computer (cf. FIGS. 6 and 7). The data logging means may also be the same memory as the one described above comprising hearing aid programs.

The data logged by the means for logging data relates to, but are not limited to, at least one of: the time per day in which the band stop filter has been switched into the hearing aid signal path, the switching events of the band stop filter, the time per day the means for presenting an audio signal is active, parameters characterizing any one of the tinnitus of the user, and parameters of the band stop filter and the audio signal.

Preferably the hearing aid further comprises means for providing feedback to the user based on said logged data. Such a feedback may e.g. be a speech signal providing a message, or a particular audio or alarm signal.

Finally, it should be noted that the above description of preferred embodiments is merely an example, and that the skilled person would know that numerous variations are possible without departing from the scope of the claims.

We claim:

1. A hearing aid adapted for alleviating tinnitus of a user, said hearing aid comprising an audio input means, a signal processing unit, an output transducer, a notch filter adapted for attenuating said audio signal at a frequency adapted to match a tinnitus of the user, switching means for switching said notch filter into a signal path formed by said audio input means, said signal processing unit and said output transducer, and out of said signal path, and switch control means, said switch control means being adapted for controlling the switching of said switching means in response to a predefined trigger event.

2. The hearing aid according to claim 1, wherein said trigger event comprises the hearing aid detecting that music is provided from the audio input.

3. The hearing aid according to claim 1, wherein said audio input means is selected from a group comprising a microphone, a telecoil, a wireless data link and a signal generator.

4. The hearing aid according to claim 1, comprising notch filter control means and tinnitus monitoring means for controlling an adaptation of notch filter parameters in response to a registered change in a perceived strength of the hearing aid users tinnitus.

5. The hearing aid according to claim 4, wherein said tinnitus monitoring means comprises means for measuring electroencephalography (EEG) signals of said user.

6. The hearing aid according to claim 4, wherein said tinnitus monitoring means comprises means for measuring magnetoencephalography (MEG) signals of said user.

7. The hearing aid according to claim 1, comprising a transposer adapted for transposing a band of frequencies, wherein said band of frequencies corresponds to a band of frequencies that are filtered out by the notch filter.

8. The hearing aid according to claim 1, comprising means for logging data regarding at least one of the following:
   an amount of time per day in which the notch filter is switched into the signal path,
   switching events of the notch filter,
   an amount of time per day said audio input means is active,
   parameters characterizing a perceived strength of said tinnitus of said user, and
   parameters characterizing settings of said notch filter, and
   wherein the hearing aid provides feedback to said user concerning the tinnitus of said user, based on said logged data.

9. The hearing aid according to claim 1, comprising speech detection means adapted for switching said notch filter out of the signal path when speech is detected.

10. A method for matching a hearing aid notch filter to a perceived tinnitus of a user of said hearing aid, comprising the steps of
   providing a hearing aid comprising a notch filter,
   using a tone presented by said hearing aid to determine a characteristic frequency of said perceived tinnitus,
   setting a center frequency of said notch filter based on said determined characteristic frequency of said perceived tinnitus,
   using sound presented by said hearing aid to determine a spectral width of the perceived tinnitus of the hearing aid user, and
   setting a spectral width of said notch filter based on said determined spectral width of the perceived tinnitus of the hearing aid user.

11. The method according to claim 10, wherein the step of determining a spectral width of the perceived tinnitus of the hearing aid user comprises the steps of presenting a first plurality of audio signals to said user and determining by selection which of said plurality of signals comprise the highest resemblance with said tinnitus.

12. The method according to claim 10, where the step of determining said characteristic frequency of said tinnitus comprises the steps of performing a rough matching procedure followed by a fine matching procedure, wherein
   said rough matching procedure comprises the steps of adjusting a frequency of said tone to be continuously or stepwise falling or rising, stopping said adjustment when said user indicates that said tone matches said tinnitus, registering the frequency thus found and performing the steps at least once with the frequency falling and at least once with the frequency rising and until a pair of frequencies, found with a falling and rising tone respectively, fall within a range of about one octave, and wherein
   said fine matching procedure comprises the steps of adjusting a frequency of a tone to be falling or rising, and reversing a direction of adjustment in response to a user decision, stopping the fine matching procedure when a predefined number of reversals have occurred, determining the characteristic tinnitus frequency of the hearing aid user based on a set of the reversal points and the frequencies corresponding to the reversal points.

13. The method according to claim 10, wherein the step of determining said characteristic frequency of said tinnitus comprises the further steps of providing said tone with a continuously or stepwise variable frequency, providing a user controlled device for adjusting said frequency until said tone matches said tinnitus, registering the frequency thus found, repeating the previous steps at least once and until two successive frequency registrations fall within a frequency range with a given bandwidth and determining the characteristic tinnitus frequency of the hearing aid user based on said frequency registrations.

14. The method according to claim 10, comprising a step of switching the notch filter into or out of a hearing aid signal path in response to detection of a trigger event.

15. The method according to claim 14, wherein said trigger event is selected from the group comprising:
   said hearing aid detecting that a sound environment is primarily music,
   said hearing aid detecting that a sound environment is primarily speech,
   said hearing aid detecting that music is streamed directly from an external unit, and
   said hearing aid detecting that specially synthesized tones generated internally in said hearing aid (fractal music) are presented to the user.

16. The method according to claim 10, comprising a step of regularly adjusting at least one of the notch filter center frequency and notch filter bandwidth based on measurements of an Auditory Steady-State Response (ASSR) of said user.

17. The method according to claim 16, wherein said ASSR is measured by means of electroencephalography (EEG) or magnetoencephalography (MEG).

18. The method according to claim 10, comprising a step of transposing a band of frequencies, wherein the band of frequencies that are transposed corresponds to a band of frequencies that are filtered out by the notch filter.

19. The method according to claim 10, comprising a step of logging parameters regarding said method in a memory unit, said parameters comprising at least one of tone output level and frequency, characteristic frequency and spectral width of the perceived tinnitus of the hearing aid user of said tinnitus, notch filter parameters, parameters regarding a switching of the notch filter into and out of a hearing aid signal path, said user's hearing threshold and UCL and parameters regarding ASSR measurements.

20. A method of adjusting a function of a hearing aid for alleviating perceived tinnitus for a user of the hearing aid, said hearing aid having audio input means, a signal processor, an output transducer, and a notch filter adapted to match the perceived tinnitus, comprising the steps of detecting a presence or absence of a predetermined trigger event, in response to detection of the presence of the trigger event, switching the notch filter into a signal path formed by said audio input means, said signal processing unit and said output transducer, and in response to detection of the absence of the trigger event, switching the notch filter out of the signal path.

* * * * *